US00PP23072P2

(12) United States Plant Patent
Graff

(10) Patent No.: US PP23,072 P2
(45) Date of Patent: Sep. 25, 2012

(54) ***HIBISCUS* PLANT NAMED 'APOLLO'**

(50) Latin Name: *Hibiscus rosa-sinensis*
Varietal Denomination: Apollo

(75) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 74 days.

(21) Appl. No.: 12/927,927

(22) Filed: Nov. 30, 2010

(51) Int. Cl.
*A01H 5/00* (2006.01)

(52) U.S. Cl. ..... Plt./257

(58) Field of Classification Search ..... Plt./257
See application file for complete search history.

*Primary Examiner* — June Hwu

(74) *Attorney, Agent, or Firm* — C. A. Whealy

(57) ABSTRACT

A new and distinct cultivar of *Hibiscus* plant named 'Apollo', characterized by its upright to somewhat outwardly spreading plant form; dense and bushy plant habit; dark green-colored leaves; freely and continuous flowering habit; large yellow and orange-colored flowers with dark red-colored centers; good flower longevity; and good garden performance.

2 Drawing Sheets

Botanical designation: *Hibiscus rosa-sinensis*.
Cultivar denomination: 'APOLLO'.

BACKGROUND OF THE INVENTION

The present invention relates to a new and distinct cultivar of *Hibiscus* plant, botanically known as *Hibiscus rosa-sinensis* and hereinafter referred to by the name 'Apollo'.

The new *Hibiscus* plant is a product of a planned breeding program conducted by the Inventor in Sabro, Denmark. The objective of the breeding program is to create new strong *Hibiscus* plants with attractive and long-lasting flowers.

The new *Hibiscus* plant originated from a cross-pollination in April, 2007 in Sabro, Denmark of *Hibiscus rosa-sinensis* 'Calypso Wind', disclosed in U.S. Plant Pat. No. 10,947, as the female, or seed, parent with a proprietary selection of *Hibiscus rosa-sinensis* identified as code number GB 2006-5009, not patented, as the male, or pollen, parent. The new *Hibiscus* plant was discovered and selected by the Inventor as a flowering plant within the progeny of the stated cross-pollination in a controlled greenhouse environment in Sabro, Denmark in April, 2008.

Asexual reproduction of the new *Hibiscus* plant by vegetative terminal cuttings in a controlled greenhouse environment in Sabro, Denmark since September, 2008, has shown that the unique features of this new *Hibiscus* plant are stable and reproduced true to type in successive generations.

SUMMARY OF THE INVENTION

Plants of the new *Hibiscus* have not been observed under all possible environmental conditions. The phenotype may vary somewhat with variations in environment conditions such as temperature and light intensity without, however, any variance in genotype.

The following traits have been repeatedly observed and are determined to be the unique characteristics of 'Apollo'. These characteristics in combination distinguish 'Apollo' as a new and distinct cultivar of *Hibiscus* plant:

1. Upright to somewhat outwardly spreading plant form.
2. Dense and bushy plant habit.
3. Dark green-colored leaves.

4. Freely and continuous flowering habit.
5. Large yellow and orange-colored flowers with dark red-colored centers.
6. Good flower longevity.
7. Good garden performance.

Plants of the new *Hibiscus* can be compared to plants of the female parent, 'Calypso Wind'. Plants of the new *Hibiscus* differ primarily from plants of 'Calypso Wind' in flower color as flowers of plants of 'Calypso Wind' have dark orange-colored flowers with dark red-colored centers. In addition, leaves of plants of the new *Hibiscus* have irregularly serrate margins whereas leaves of plants 'Calypso Wind' have crenate margins.

Plants of the new *Hibiscus* can be compared to plants of the male parent selection. Plants of the new *Hibiscus* differ primarily from plants of the male parent selection in flower longevity as flowers of plants of the new *Hibiscus* last about three to four days whereas flowers of plants of the male parent selection last about one or two days. In addition, plants of the new *Hibiscus* and the male parent selection differ in flower shape.

Plants of the new *Hibiscus* can be compared to plants of the *Hibiscus rosa-sinensis* 'Cairo Apricot', not patented. In side-by-side comparisons conducted in Sabro, Denmark, plants of the new *Hibiscus* differed from plants of 'Cairo Apricot' in the following characteristics:

1. Plants of the new *Hibiscus* had broader flower buds than plants of 'Cairo Apricot'.
2. Flowers of plants of the new *Hibiscus* lasted about three to four days whereas flowers of plants of 'Cairo Apricot' lasted about one day.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Apollo' grown in a container.

The photograph on the second sheet are close-up views of typical developing flower buds and a fully opened flower of 'Apollo'.

DETAILED BOTANICAL DESCRIPTION

The aforementioned photographs and following observations, measurements and values describe plants grown during the summer in 13-cm containers in a glass-covered greenhouse in Sabro, Denmark and under conditions which closely approximate commercial *Hibiscus* production. During the production of the plants, day temperatures ranged from 20° C. to 25° C., night temperatures ranged from 19° C. to 21° C. and light levels ranged from 40 to 50 klux. Plants were pinched one time about seven weeks after planting and were 24 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Apollo'.

Parentage:

*Female, or seed, parent.*—*Hibiscus rosa-sinensis* 'Calypso Wind', disclosed in U.S. Plant Pat. No. 10,947.

*Male or pollen parent.*—Proprietary selection of *Hibiscus rosa-sinensis* identified as code number GB 2006-5009, not patented.

Propagation:

*Type.*—By vegetative terminal cuttings.

*Time to initiate roots, summer.*—About three weeks at temperatures of 24° C.

*Time to initiate roots, winter.*—About four weeks at temperatures of 24° C.

*Time to produce a rooted young plant, summer.*—About seven weeks at temperatures of 24° C.

*Time to produce a rooted young plant, winter.*—About eight weeks at temperatures of 24° C.

*Root description.*—Medium in thickness, fleshy; color, close to 158A.

*Rooting habit.*—Freely branching; dense.

Plant description:

*Plant form and growth habit.*—Upright to somewhat outwardly spreading plant form; moderately vigorous growth habit.

*Branching habit.*—Freely branching, usually about four to six lateral branches develop; pinching enhances lateral branch development; dense and bushy plant habit.

*Plant height.*—About 35 cm to 55 cm.

*Plant diameter* (*area of spread*).—About 30 cm to 50 cm.

Lateral branch description:

*Length.*—About 15 cm to 25 cm.

*Diameter.*—About 3 mm to 6 mm.

*Internode length.*—About 1 cm to 5 cm.

*Strength.*—Strong.

*Texture.*—Woody.

*Color.*—Close to N199A and 197A.

Foliage description:

*Arrangement.*—Alternate, simple.

*Length.*—About 8 cm to 12 cm.

*Width.*—About 8 cm to 10 cm.

*Shape.*—Cordate.

*Apex.*—Cuspidate.

*Base.*—Cordate.

*Margin.*—Irregularly serrate.

*Texture, upper and lower surfaces.*—Smooth, glabrous.

*Luster, upper and lower surfaces.*—Slightly glossy.

*Venation pattern.*—Pinnate; arcuate.

*Color.*—Developing leaves, upper surface: Close to 146A. Developing leaves, lower surface: Close to 146B. Fully expanded leaves, upper surface: Close to 147A; venation, close to 144B. Fully expanded leaves, lower surface: Close to 146B; venation, close to 144C.

*Petiole.*—Length: About 3 cm to 5 cm. Diameter: About 2 mm to 3 mm. Texture, upper surface: Pubescent. Texture, lower surface: Smooth, glabrous. Color, upper surface: Close to N199A. Color, lower surface: Close to N199A and 146A.

Flower description:

*Flower shape and arrangement.*—Rounded flowers with imbricate petals arranged singly at terminal leaf axils; continuous and freely flowering habit with numerous flower buds and/or open flowers per plant at one time; flowers face mostly upright.

*Fragrance.*—None detected.

*Flower longevity.*—Good flower longevity, flowers last for about three to four days; flowers persistent.

*Natural flowering season.*—Usually spring and summer or during periods of warm weather; plants flower year-round in the greenhouse; plants begin flowering about 13 to 15 weeks after pinching.

*Flower diameter.*—About 16 cm to 20 cm.

*Flower length* (*height*).—About 10 cm to 15 cm.

*Flower bud.*—Rate of opening: Flowers buds open in about three days. Length: About 6 cm to 9 cm. Diameter: About 2 cm to 4 cm. Shape: Ovate to lanceolate. Color: Towards the base, close to 29B; towards the apex, close to 1B.

*Petals.*—Arrangement: Corolla consists of five imbricate petals in a single whorl. Length: About 10 cm to 12 cm. Width: About 8 cm to 9 cm. Shape: Roughly spatulate. Apex: Rounded. Base: Attenuate. Margin: Entire; undulate. Texture, upper surface: Glabrous; velvety. Texture, lower surface: Glabrous; satiny. Color: When opening, upper surface: Towards the margin, close to 15B; center, close to N30A; towards the base, close to 53D; at the base, close to 53A. When opening, lower surface: Towards the margin, close to 16B; towards the base, close to 29B. Fully opened, upper surface: Towards the margin, close to 15B; center, close to N30A; towards the base, close to 53D; at the base, close to 53A; venation, towards the margin, close to N30A and 15B; venation, center, close to 15B; venation, towards the base and at the base, close to 53D and 53A. Fully opened, lower surface: Close to 16B to 16C.

*Sepals.*—Appearance: Five sepals fused into a campanulate-shaped calyx. Length: About 3 cm to 3.5 cm. Width: About 1.5 cm. Shape: Lanceolate. Apex: Acuminate. Anther shape: Rounded to ovate. Anther length: About 1 mm to 2 mm. Anther color: Close to 12C. Amount of pollen: Abundant. Pollen color: Close to 12A. Gynoecium: Pistil length: About 10 cm. Style length: About 9 cm. Style texture: Smooth, waxy. Style color: Towards the apex, close to 68C;

mid-section, close to 53C; towards the base, close to 53A. Stigma appearance: Five-parted, rounded. Stigma color: Close to 14A. Ovary color: Close to 145A and 2C.

*Seeds*.—Quantity produced per flower: About 1 to 16. Length: About 4 mm to 5 mm. Margin: Entire. Texture, upper surface: Rough. Texture, lower surface: Smooth. Color, upper surface: Close to 144A to 144C. Color, lower surface: Close to 144B.

*Peduncles*.—Length: About 2 cm to 5 cm. Diameter: About 2 mm to 3 mm. Angle: Mostly upright. Strength: Strong. Texture: Pubescent. Color: Close to 144A.

*Reproductive organs*.—Androecium: Stamen number: Numerous, about 100. Filament length: About 3 cm. Filament color: Close to 49A and 11D. Diameter: About 3 mm to 4 mm. Color: Close to N200A.

Garden performance: Plants of the new *Hibiscus* have been observed to have good garden performance and to tolerate rain, wind and temperatures ranging from about 1° C. to about 30° C.

Pathogen/pest resistance: Plants of the new *Hibiscus* have not been observed to be resistant to pathogens and pests common to *Hibiscus*.

It is claimed:

1. A new and distinct *Hibiscus* plant named 'Apollo' as illustrated and described.

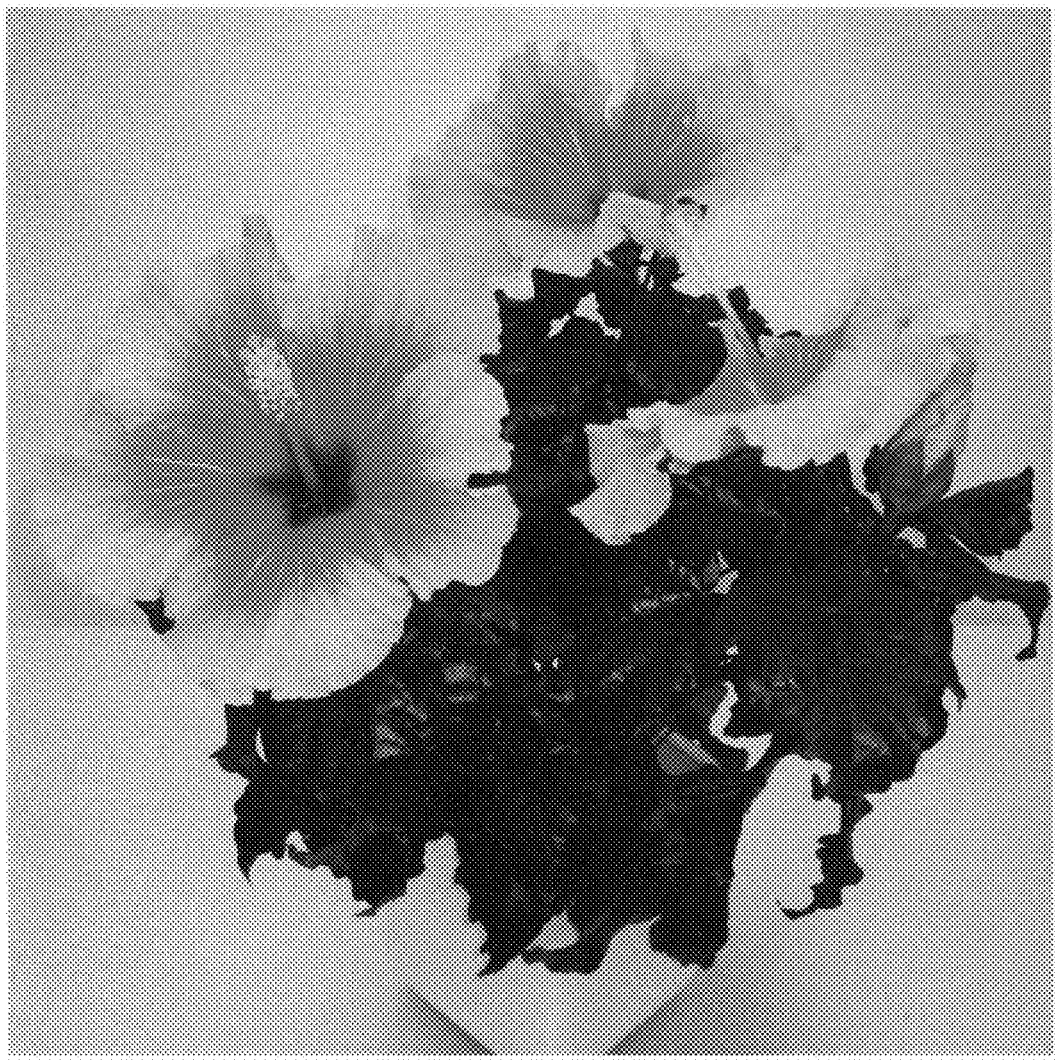

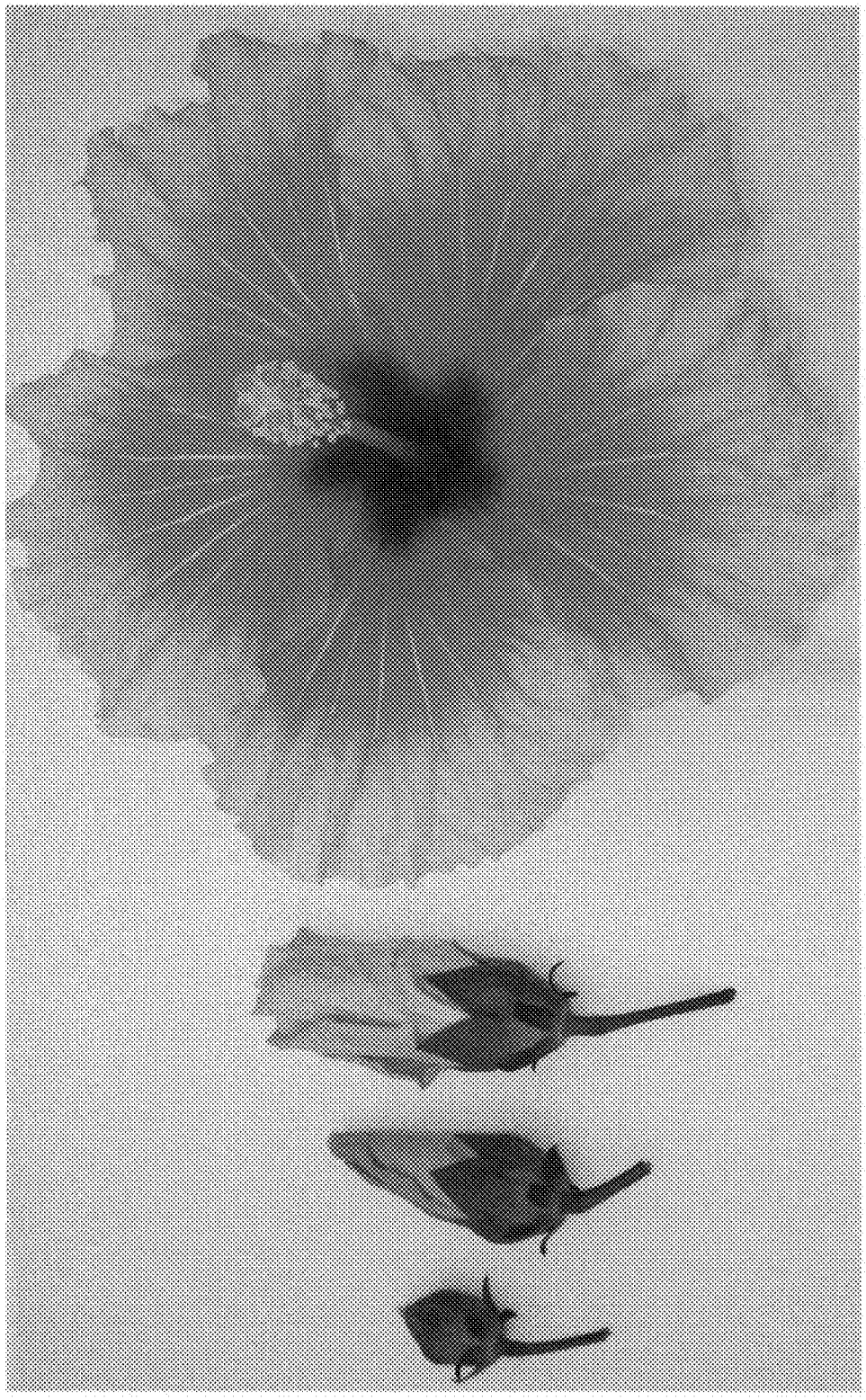

* * * * *